United States Patent [19]

Findeisen et al.

[11] 4,069,252

[45] Jan. 17, 1978

[54] PROCESS FOR THE PREPARATION OF CERTAIN ACYL CYANIDE COMPOUNDS

[75] Inventors: Kurt Findeisen, Odenthal; Wilfried Draber, Wuppertal; Herbert Schwarz, Leverkusen, all of Germany

[73] Assignee: Bayer Aktiengesellschaft, Leverkusen, Germany

[21] Appl. No.: 693,827

[22] Filed: June 4, 1976

[30] Foreign Application Priority Data

June 25, 1975 Germany .............................. 2528211

[51] Int. Cl.² .................... C07C 63/04; C07C 120/04
[52] U.S. Cl. ............................................... 260/545 R
[58] Field of Search ....................... 260/310 R, 545 R

[56] References Cited

U.S. PATENT DOCUMENTS

| | | | |
|---|---|---|---|
| 3,234,265 | 2/1966 | Krekeler et al. | 260/545 R |
| 3,637,843 | 1/1972 | Patton | 260/545 R |
| 3,950,416 | 4/1976 | Patton | 260/545 R |

OTHER PUBLICATIONS

Journal of the Chemical Society, vol. 127, July 1925, pp. 1633 & 1635.

*Primary Examiner*—Donald B. Moyer
*Attorney, Agent, or Firm*—Burgess, Dinklage & Sprung

[57] ABSTRACT

Acyl cyanide compounds of the formula

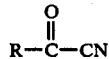

are prepared by reacting an acid halide of the formula

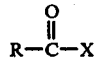

with anhydrous hydrocyanic acid in the presence of a tertiary amine at a temperature between −70° and +100° C. R can be hydrocarbyl or substituted hydrocarbyl and X is halogen.

13 Claims, No Drawings

PROCESS FOR THE PREPARATION OF CERTAIN ACYL CYANIDE COMPOUNDS

The present invention relates to a process for the preparation of certain acyl cyanide compounds. Such compounds are useful as starting materials for the synthesis of herbicides.

It is known that acyl cyanides can be prepared by reacting acyl halides with metal cyanides (see, Angw. Chem. 68, 425–448 (1956)). However, this process has a number of disadvantages. Thus, for example, it is involved and can be carried out industrially only with difficulty since it is a two-phase reaction in which a solid is reacted with a liquid or with a substance which is present in solution. However, the reaction does not give a single reaction product but a mixture of substances which is difficult to separate and which also contains, in addition to the particular acyl cyanide, a relatively large amount of a corresponding dimer. Accordingly, the yields of acyl cyanide are relatively low. A further disadvantage of this process is that the wash water, which is obtained during working up, has to be subjected to thorough purification before it is discharged because it still contains considerable amounts of highly toxic metal cyanides, which are used in excess in the reaction.

Furthermore, it is known that aroyl cyanides can be synthesized by reacting arylcarboxylic acid chlorides with hydrocyanic acid, in the presence of pyridine as an acid-binding agent, in absolute ether (see Angew. Chem. 68, 425–448 (1956)). However, this process also is subject to several disadvantages. Thus, firstly, it is not generally applicable. Moreover, it is technically fairly involved because working with pyridine, which is highly toxic, and with ether, which is readily inflammable, requires particularly strict safety precautions. Furthermore, in this case also, thorough purification of the wash water obtained during working up is unavoidable because of the pyridine dissolved therein. The fact that a considerable amount of dimeric aroyl cyanide forms during the reaction is also disadvantageous since, as a result, both the yield of the aroyl cyanide is greatly reduced and the isolation thereof is made more difficult.

The present invention provides a process for the preparation of an acyl cyanide of the general formula.

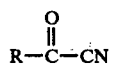 (I), in which
R represents optionally substituted alkyl with 1 to 8 carbon atoms, optionally substituted cycloalkyl with 3 12 carbon atoms or optionally substituted aryl or represents an optionally substituted 5-membered or 6-membered heterocyclic radial, which additionally can also be fused to a benzene ring, in which an acid halide of the general formula

 (II)

in which
R has the abovementioned meaning and
X represents halogen, preferably fluorine, chlorine or bromine, is reacted with anhydrous hydrocyanic acid in the presence of an aliphatic, araliphatic or alicyclic tertiary amine, and optionally in the presence of a non-polar aprotic diluent, at temperatures between −70° C and +100° C.

Preferably, R represents straight-chain or branched alkyl with 1 to 4 carbon atoms, which alkyl radical can carry one or more substituents selected from alkoxy with 1 to 4 carbon atoms carbalkoxy with 1 to 4 carbon atoms in the alkoxy group, nitro, nitrile and halogen (such as, for example, fluorine, chlorine, bromine or iodine); cycloalkyl which has 5 or 6 carbon atoms in the ring system and which optionally carries one or more substituents selected from alkyl, alkoxy and carbalkoxy, with, in each case, up to 4 carbon atoms, and nitro, nitrile and halogen (such as, for example, fluorine, chlorine and bromine); aryl (expecially phenyl or naphthyl), which optionally carries one or more substituents selected from alkyl, alkoxy and carbalkoxy, with, in each case, up to 4 carbon atoms, and nitro and halogen (such as, for example, fluroine, chlorine and bromine); or a 5-membered or 6-membered heterocyclic radical, which optionally carries one or more substituents selected from alkyl, alkoxy and carbalkoxy, with, in each case, up to 4 carbon atoms, and nitro, nitrile and halogen (such as, for example, fluorine, chlorine and bromine), which can contain in the ring 1 to 3 hetero-atoms selected from oxygen, sulphur and nitrogen, and which can be fused to a benzene ring. Examples of such heterocyclic radicals R are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

It is to be regarded as extremely surprising that acyl cyanides of the formula (I) are accessible in high yield and excellent purity by the process according to the invention, since, in view of the known state of the art, it was to be expected that the same difficulties would arise with this process as with the analogous reaction of arcylcarboxylic acid chlorides with hydrocyanic acid in the presence of pyridine. In particular, it was in no way to be foreseen that it is possible to a very great extent to suppress the formation of undesired dimers by replacing the pyridine by an aliphatic, araliphatic or alicyclic tertiary amine.

The process according to the invention has a number of advantages. Thus, it is not restricted to the synthesis of a few specific compounds but can be very widely employed. Quite apart from this, it can also be carried out on an industrial scale in a relatively simple manner. With the process according to the invention, the acyl cyanides can be obtained as already mentioned, in high yield and excellent purity and almost free from objectionable by-products. An additional important advantage of the process according to the invention is that working up presents no problems. The crystalline hydrohalides formed in the course of the reaction can be filtered off without difficulties after stripping off excess hydrocyanic acid, while the residual filtrate is subjected to a simple fractional distillation. Hydrocycanic acid and solvent which are present in excess are also recovered and therefore need not signify a pollution of the environment. The process according to the invention thus represents a valuable enrichment of the art.

If benzoyl chloride and anhydrous hydrocyanic acid are used as the starting material and dimethylbenzylamine is used as tertiary amine, the course of the reaction can be represented by the following equation:

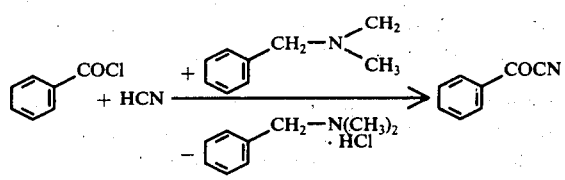

The acid halides of the formula (II) which are to be used as starting materials are known or can be prepared according to methods which are known in principle. Examples of halides of the formula (II) which may be mentioned are: acetyl chloride, acetyl bromide, propionyl chloride, propionyl bromide, cyclohexanecarboxylic acid chloride or acid bromide, cyclopentanecarboxylic acid chloride or acid bromide, cyclopentanecarboxylic acid chloride or acid bromide, benzoyl fluoride, benzoyl bromide, benzoyl chloride, m-chloro-benzoyl chloride, 3,5-dichlorobenzoyl chloride, naphthalene-1-carboxylic acid chloride and 1-phenyl-5-pyrazolone-3-carboxylic acid chloride. Benzoyl chloride may be mentioned as a particularly preferred acid chloride.

As already mentioned, aliphatic, araliphatic or alicyclic tertiary amines are used as acid-binding agents when carrying out the process according to the invention. In the present case, the preferred aliphatic tertiary amines are those compounds in which the nitrogen atom is bonded to three alkyl radicals and each of the alkyl radicals contains 1 to 4 carbon atoms. Examples of such tertiary amines are triethylamine and tri-n-propylamine. In the present case, the preferred araliphatic tertiary amines are those compounds in which the nitrogen atom is substituted by an aralkyl group and by two alkyl groups each with 1 to 4 carbon atoms. Examples of such tertiary amines are dimethyl benzylamine, diethylbenzylamine and diisopropylbenzylamine. In the present case, the preferred alicyclic tertiary amines are those compounds in which the nitrogen atom carries a cycloalkyl group with 5 to 7 carbon atoms and also two alkyl groups, each with 1 to 4 carbon atoms, and also those compounds in which the nitrogen atom is included in one or two cycloalkyl or cycloalkenyl groups. Examples of such tertiary amines are dimethylamino-cyclohexane, 1,4-diazobicyclo-(2,2,2)-octane, 1,8-diazo-bicyclo-(5,4,0)-undec-7-ene and 1,5-diaza-bicyclo-(4,3,0)-non-5ene.

Possible diluents, which can be employed when carrying out the process according to the invention, are all the nonpolar aprotic solvents, especially aromatic hydrocarbons, such as benzene, toluene, xylene and mesitylene, and also aliphatic hydrocarbons, such as pentane, hexane, heptane, octane, cyclohexane, methylcyclohexane, cycloheptane and wash benzine.

In principle it is also possible to carry out the reaction according to the invention in weakly polar solvents, such as, for example, ethyl acetate, ether or acetonitrile. However, in this case the desired acyl cyanide is formed in a lower yield, while the proportion of undesired dimeric acyl cyanide increases.

The process according to the invention can be carried out particularly advantageously when the anhydrous hydrocyanic acid, which acts as a reactant, is used in a large excess. In this case the addition of a further diluent is unnecessary.

The reaction temperature can be varied within a relatively wide range, that is between −70° C and +100° C. The reaction is preferably carried out at temperatures between −40° C and +20° C.

In general, the process according to the invention is carried out under normal pressure. Although it is possible to increase the pressure this does not, however, result in any substantial advantages.

When carrying out the process according to the invention, 1 to 2 moles of anhydrous hydrocyanic acid and 1 mole of an aliphatic, araliphatic or alicyclic tertiary amine are generally employed per mole of the acid halide of the formula (II). If the hydrocyanic acid is simultaneously used as the solvent, it is appropriate to employ 4 moles or an even greater excess of anhydrous hydrocyanic acid per mole of the acid halide of the formula (II).

Usually, working up is carried out, after the reaction has ended, by first stripping off any excess hydrocyanic acid which may be present and condensing this in a receiver, then filtering off the amine hydrohalide, which is obtained in a crystalline form, and subjecting the residual filtrate to fractional vacuum distillation. In general, the reaction products are already obtained in high purity by this means. If necessary, they can be recrystallized or distilled again, for further purification. If the reaction according to the invention is carried out in an excess of hydrocyanic acid but in the absence of additional solvents, working up is then carried out by again first stripping off the excess hydrocyanic acid and condensing this in a receiver, then taking up the residue in an inert organic solvent, filtering off the crystalline amine hydrohalide and subjecting the residual filtrate to fractional distillation. In some case it is also possible to subject the residue obtained after stripping off the hydrocyanic acid to fractional distillation direct, without previously separating off the crystalline amine hydrohalide.

In a particular embodiment of the process, the reaction according to the invention can also be carried out as a continuous process. For this purpose, for example, a cooled solution of the acid halide of the formula (II) and hydrocyanic acid in xylene are mixed with the aid of a second cooled solution of the tertiary amine in xylene and the mixture is made to react. Thereafter, the reaction mixture is first freed from excess hydrocyanic acid by warming under reduced pressure and is then fed continuously to a closed vacuum filter and the filtrate thus obtained is subjected to fractional vacuum distillation.

The acyl cyanides of the formula (I), which can be prepared by the process according to the invention, are valuable starting materials for the synthesis of 1,2,4-triazin-5-ones, which prossess outstanding herbicidal properties (see German Offenlegungsschrift No. (German Published Specification) 2,224,161).

Thus, for example, 3-methyl-4-amino-6-phenyl-1,2,4-triazin-5-one of the formula

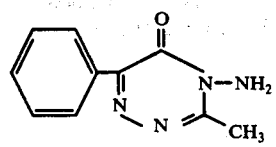

can be prepared, in a first stage, benzoyl cyanide is reacted, in the presence of concentrated hydrochloric acid, with an alkanol and the phenylglyoxylic acid ethyl ester thus formed is reacted, in a second stage, with acetyl hydrazine, whereupon the 2-acetylhydrazone of 1-phenylglyoxylic acid ethyl ester is formed, which, in a third stage, is converted, by means of hydrate in the presence of pyridine, to the abovementioned end product. This multi-stage synthesis can be represented by equations, as follows:

1st stage:

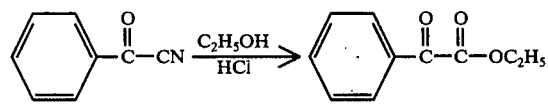

2nd stage:

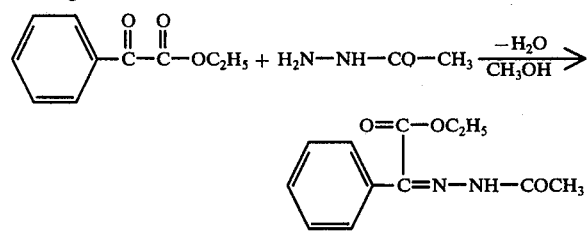

3rd stage:

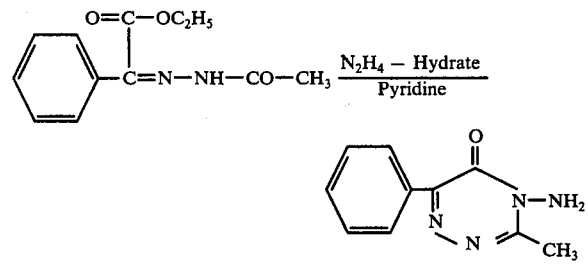

The process according to the invention is illustrated by the preparative examples which follow:

EXAMPLE 1

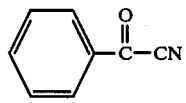 (1)

Process variant (a)

703 g (5 moles) of benzoyl chloride and 400 ml (10 moles) of anhydrous hydrocyanic acid were dissolved in 2,000 ml of xylene, while cooling, in a 10 litre four-necked flask fitted with a stirrer, thermometer, reflux condenser and dropping funnel. At an internal temperature of −40° C, a solution of 675 g (5 moles) of dimethylbenzylamine in 500 ml of xylene was added dropwise, while cooling, in the course of one hour at such a rate that the temperature of the reaction mixture did not exceed −40° C. When the addition was complete, the mixture was stirred for a further 10 minutes at −40° C and the excess hydrocyanic acid was then distilled, under a waterpump vacuum, into a cooled receiver. When, after about 2 hours, a pressure of 20 mm Hg had been reached, air was let into the system and the dimethylbenzylamine hydrochloride, which had already been obtained in a crystalline form during the reaction, was filtered off and rinsed with 500 ml of xylene. The combined xylene solutions were subjected to fractional distillation, the xylene employed being substantially recovered. In this way 630 g (96% of theory) of benzoyl cyanide with a melting point of 31° C were obtained.

Process variant (b)

67.5 g (0.5 mole) of dimethylbenzylamine were added dropwise, at −10° C, while cooling, to a mixture of 70.3 g (0.5 mole) of benzoyl chloride and 80 ml (2 moles) of anhydrous hydrocyanic acid at such a rate that the temperature of the reaction mixture did not exceed −10° C. When the addition was complete, the mixture was stirred for a further 10 minutes at −10° C and the excess hydrocyanic acid was then distilled off under a waterpump vacuum. Further working up was carried out by adding 30 ml of xylene to the residue, filtering off the crystalline dimethylbenzylamine hydrochloride and subjecting the filtrate to fractional vacuum distillation.

However, it was also possible to subject the residue obtained after stripping off the excess hydrocyanic acid to fractional distillation without the prior addition of xylene.

In this way 60.5 g (92% of theory) of benzoyl cyanide with a melting point of 31° C were obtained.

Process variant (c)

703 g (5 moles) of benzoyl chloride and 200 ml (5 moles) of anhydrous hydrocyanic acid were added to 2,000 ml of xylene and the mixture was cooled to −20° C in a storage vessel. In a second storage vessel, 675 g (5 moles) of dimethylbenzylamine were dissolved in 500 ml of xylene and this solution was also cooled to −20° C. The two mixtures were then combined with the aid of a metering pump. Subsequently, the excess hydrocyanic acid was removed by warming to 25° C under reduced pressure and the residue was fed continuously to a vacuum pressure filter. After neutralization, the resulting dimethylbenzylamine hydrochloride was re-employed in the reaction. The filtrate was subjected to fractional vacuum distillation.

In this way 635 g (97% of theory) of benzoyl cyanide with a melting point of 31° C were obtained.

EXAMPLE 2

 (2)

A solution of 135 g (1 mole) of dimethylbenzylamine in 100 ml of toluene was added dropwise, at −20° C, while cooling, in the course of 30 minutes to a mixture of 170 g (1 mole) of para-methoxybenzoyl chloride and 50 g of anhydrous hydrocyanic acid in 400 ml of toluene at such a rate that the internal temperature did not rise above −20° C during the addition. When the addition was complete, the mixture was stirred for a further 10 minutes at −20° C and excess hydrocyanic acid was then distilled, under a waterpump vacuum, into a cooled receiver. The residue was recrystallized from a mixture of benzene and ligroin. In this way 128 g (77% of theory) of para-methoxybenzoyl cyanide with a melting point of 63° C were obtained.

EXAMPLE 3

 (3)

A solution of 163 g (1 mole) of diethylbenzylamine in 150 ml of toluene was added dropwise, at −20° C, while stirring and cooling, to a mixture of 123 g (1 mole) of acetyl bromide and 30 g of anhydrous hydrocyanic acid in 300 ml of toluene at such a rate that the internal temperature did not rise above −20° C during the addition. When the addition was complete, the mixture was stirred for a further 10 minutes at −20° C and the excess hydrocyanic acid was then distilled, under a waterpump vacuum, into a cooled receiver. The crystalline diethylbenzylamine hydrobromide was filtered off from the residual reaction mixture. On concentrating the filtrate, 43 g (62% of theory) of acetyl cyanide with a boiling point of 93° C were obtained.

EXAMPLE 4

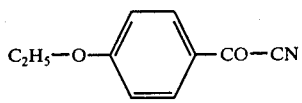
(4)

A solution of 135 g (1 mole) of dimethylbenzylamine in 100 ml of benzene was added dropwise, at −2° C, while cooling, in the course of 30 minutes to a mixture of 184 g (1 mole) of para-ethoxybenzoyl chloride and 54 g (2 moles) of anhydrous hydrocyanic acid in 300 ml of benzene at such a rate that the internal temperature did not rise above −20° C during the addition. When the addition was complete, the mixture was stirred for a further 10 minutes at −20° C and the excess hydrocyanic acid was then distilled, under a waterpump vacuum, into a cooled receiver. Dimethylbenzylamine hydrochloride, which was obtained in a crystalline form, was filtered off from the residual reaction mixture. The filtrate was subjected to fractional vacuum distillation. In this way 152 g (87% of theory) of para-ethoxybenzoyl cyanide with a melting point of 43° C were obtained.

Preparation of
3-methyl-4-amino-6-phenyl-1,2,4-triazin-5-one, starting from benzoyl cyanide

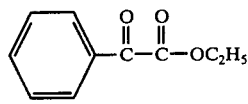
(a)

A solution of 1 mole of benzoyl cyanide in 10 moles of ethanol was boiled under reflux, in the presence of HCl, for 5 hours. Excess ethanol was then distilled off and the residue was subjected to fractional distillation.

In this way, phenylglyoxylic acid ethyl ester was obtained.

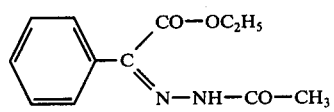
(b)

178 g (1 mole) of phenylglyoxylic acid ethyl ester and 74 g (1 mole) of well dried acetylhydrazine were dissolved in 200 ml of methanol and the solution was boiled under reflux for 20 minutes. The solvent was then distilled off and the residual reaction mixture was cooled to 0° C and triturated with ether. The yellowish crystals which separated out were filtered off, washed with ether/petroleum ether and dried.

190 g (81% of theory) of the 2-acetylhydrazine of 1-phenyl-glyoxylic acid ethyl ester with a melting point of 89° C were obtained.

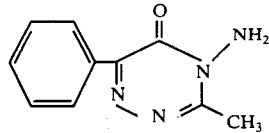
(c)

23.4 g (0.1 mole) of the 2-acetylhydrazone of 1-phenylglyoxylic acid ethyl ester and 10.3 ml (0.2 mole) of hydrazine hydrate were mixed with 100 ml of pyridine, which had been dried over potassium hydroxide, and the mixture was stirred under reflux at a temperature of 100° C for 45 minutes. On subsequent cooling, the mixture solidified to a firm slurry, which was treated with 100 ml of water and stirred for several hours. The undissolved material was filtered off, washed well with water and dried. 7.1 g (36% of theory) of 3-methyl-4-amino-6-phenyl-1,2,4-triazin-5-one with a melting point of 167°–169° C were thus obtained.

It will be understood that the specification and examples are illustrative but not limitative of the present invention and that other embodiments within the spirit and scope of the invention wil suggest themselves to those skilled in the art.

What is claimed is:

1. In a process for the preparation of an acyl cyanide compound of the general formula

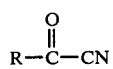

in which
  R is alkyl of from 1 to 4 carbon atoms, or phenyl optionally substituted by alkoxy of from 1 to 4 carbon atoms
which process comprises reacting an acid halide of the general formula

in which
  R is identified as above and
  X represents halogen,
  with anhydrous hydrocyanic acid
which improvement comprises carrying out the reaction in the presence of an aliphatic, araliphatic or alicyclic tertiary amine, at a temperature between −70° C and +100° C.

2. Improvement as claimed in claim 1, in which the reaction is effected in the presence of a non-polar, aprotic solvent.

3. Improvement as claimed in claim 1 in which the solvent is an aromatic or aliphatic hydrocarbon.

4. Improvement as claimed in claim 3 in which the solvent is xylene, toluene or benzene.

5. Improvement as claimed in claim 1 in which 1 to 2 moles of hydrocyanic acid and 1 mole of the tertiary amine are employed per mole of the acid halide.

6. Improvement as claimed in claim 1 in which an excess of the anhydrous acid is used as a solvent.

7. Improvement as claimed in claim 6 in which 1 mole of the teriary amine and at least 4 moles of hydrocyanic acid are employed per mole of the acid halide.

8. Improvement as claimed in claim 1 in which the tertiary amine is a trialkylamine of from 1 to 4 carbon atoms in each alkyl group, a dialkyl-benzylamine of from 1 to 4 carbon atoms in each alkyl group, a cycloalkyl-dialkylamine of from 5 to 7 carbon atoms in the cycloalkyl group and from 1 to 4 carbon atoms in each alkyl group or an amine in which the nitrogen atom is included in one or two cycloalkyl or cycloalkenyl groups.

9. Improvement as claimed in claim 8 in which the tertiary amine is dimethylbenzylamine or diethylbenzylamine.

10. Improvement as claimed in claim 1 in which the reaction is effected at between $-40°$ and $+20°$ C.

11. Improvement as claimed in claim 1 which R is phenyl.

12. A process as claimed in claim 1 in which X is fluorine, chlorine or bromine.

13. Improvement as claimed in claim 1 in which the acid halide is acetyl chloride, acetyl bromide, propionyl chloride, propionyl bromide, benzoyl fluoride, benzoyl bromide, benzoyl chloride, p-methoxy-benzoyl chloride or p-ethoxy-benzoyl chloride.

* * * * *